United States Patent
Fujii et al.

(10) Patent No.: US 7,561,259 B2
(45) Date of Patent: Jul. 14, 2009

(54) LAMINATION STATUS INSPECTING APPARATUS, LAMINATION STATUS INSPECTING METHOD, AND RECORDING MEDIUM STORING LAMINATION STATUS DETECTING PROGRAM

(75) Inventors: Asako Fujii, Kawasaki (JP); Tomonobu Takashima, Kawasaki (JP); Jou Tanji, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 12/149,516

(22) Filed: May 2, 2008

(65) Prior Publication Data

US 2008/0204725 A1    Aug. 28, 2008

Related U.S. Application Data

(63) Continuation of application No. PCT/JP2005/020372, filed on Nov. 7, 2005.

(51) Int. Cl.
*G01B 11/00* (2006.01)

(52) U.S. Cl. ............................. 356/72; 356/614; 156/64

(58) Field of Classification Search .................... 356/72, 356/614; 156/64
See application file for complete search history.

(56) References Cited

U.S. PATENT DOCUMENTS

| | | | |
|---|---|---|---|
| 5,094,539 | A | 3/1992 | Komoriya et al. |
| 5,115,142 | A | 5/1992 | Taguchi et al. |
| 5,260,771 | A | 11/1993 | Komoriya et al. |
| 5,432,608 | A | 7/1995 | Komoriya et al. |
| 2006/0108048 | A1 * | 5/2006 | Engelbart et al. ............. 156/64 |

FOREIGN PATENT DOCUMENTS

| | | |
|---|---|---|
| JP | 2-105002 | 4/1990 |
| JP | 3-75502 | 3/1991 |
| JP | 3-245003 | 10/1991 |
| JP | 2001-183113 | 7/2001 |

* cited by examiner

*Primary Examiner*—F. L Evans
(74) *Attorney, Agent, or Firm*—Staas & Halsey LLP

(57) ABSTRACT

A lamination status inspecting apparatus inspects a lamination status of adjacent sheets, and includes a first illumination unit that irradiates a portion where sheets are adjacent to each other with light from a predetermined direction, a second illumination unit that irradiates with light from a direction opposite to a direction of the first illumination unit, an imaging unit that picks up an image of the portion, and an imaging control unit that controls the imaging unit to pick up a first image of the portion by lighting the first illumination unit, and controls the imaging unit to pick up a second image of the portion by lighting the second illumination unit.

8 Claims, 14 Drawing Sheets

LAMINATION STATUS INSPECTING APPARATUS 200

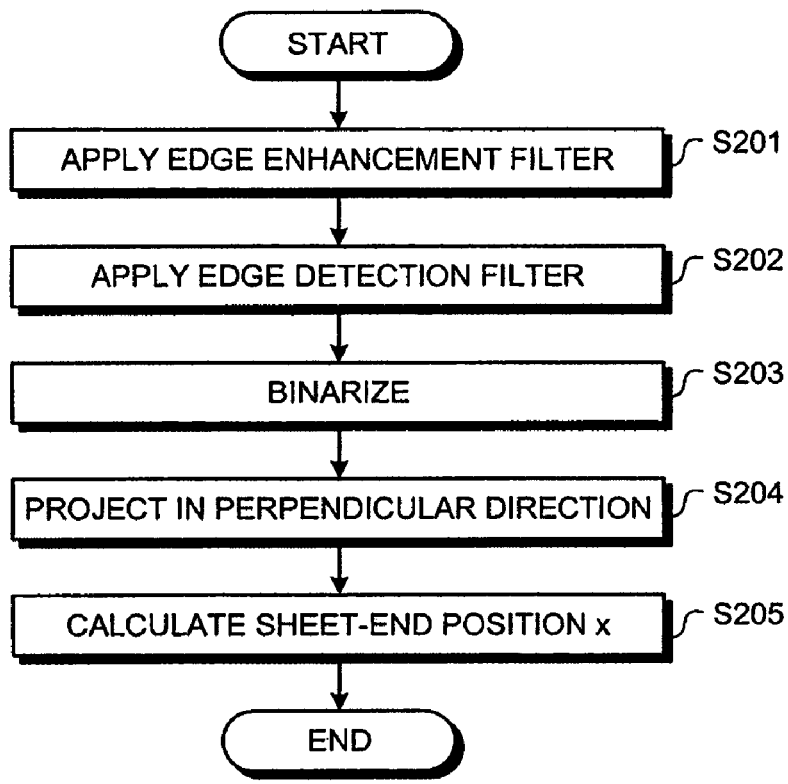

FIG.14

| $k_{i-1,j-1} = 1$ | $k_{i,j-1} = 0$ | $k_{i+1,j-1} = -1$ |
|---|---|---|
| $k_{i-1,j} = 2$ | $k_{i,j} = 0$ | $k_{i+1,j} = -2$ |
| $k_{i-1,j+1} = 1$ | $k_{i,j+1} = 0$ | $k_{i+1,j+1} = -1$ |

FIG.15

| $k_{i-1,j-1} = -1$ | $k_{i,j-1} = 0$ | $k_{i+1,j-1} = 1$ |
|---|---|---|
| $k_{i-1,j} = -2$ | $k_{i,j} = 0$ | $k_{i+1,j} = 2$ |
| $k_{i-1,j+1} = -1$ | $k_{i,j+1} = 0$ | $k_{i+1,j+1} = 1$ |

LAMINATION STATUS INSPECTING APPARATUS, LAMINATION STATUS INSPECTING METHOD, AND RECORDING MEDIUM STORING LAMINATION STATUS DETECTING PROGRAM

This application is a continuing application, filed under 35 U.S.C. § 111(a), of International Application PCT/JP2005/020372, filed Nov. 7, 2005, the contents of which are incorporated herein by reference.

BACKGROUND OF THE INVENTION

1. Field of the Invention

The present invention relates to a compact, lamination status inspecting apparatus, a lamination status inspecting method, and a lamination status detecting program for inspecting a lamination status of adjacent sheets.

2. Description of the Related Art

In recent years, a material called prepreg is widely used in fields of aerospace and sports, in which materials are required to be light-weight and of high performance. Prepreg is a sheet-like, in-process, molding material in a semi-cured state manufactured by impregnating a carbon fiber with a thermosetting resin. Plural prepreg sheets are united together to form a multilayer laminate which is then molded through thermal hardening.

If a prepreg sheet overlaps with an adjacent prepreg sheet during a lamination process, or a gap between adjacent prepreg sheets is wide, strength of a finished molded product could be insufficient. Therefore, in the lamination process, it is necessary to check an overlap of the adjacent sheets and an amount of gap therebetween so as to inspect if the sheets are properly adhered with each other.

To detect an overlap of adjacent sheets and to measure a gap amount, a level difference between the sheets needs to be detected. As a technique for detecting a level difference, an apparatus is disclosed in Japanese Patent Application Laid-open No. 2001-183113. The disclosed apparatus forms a shade of a step using two illuminations, receives reflected lights of the illuminations respectively by two sensors utilizing characteristic of reflection and transmission of a mirror thereby obtaining two images, and detects a level difference in inspected objects based on a difference between the two images.

Conventionally, whether adjacent sheets are properly adhered with each other is manually inspected. However, this procedure has a problem in that a person cannot thoroughly inspect the sheets because of their significantly large lamination areas and that the check requires high manpower cost and time.

Further, the apparatus of Japanese Patent Application Laid-open No. 2001-183113 has problems in that the apparatus has a large size because of a mirror, two light-receiving sensors, and lenses, and that high precision is required in positioning of the two light-receiving sensors because of the use of a difference.

SUMMARY OF THE INVENTION

It is an object of the present invention to at least partially solve the problems in the conventional technology.

A lamination status inspecting apparatus according to one aspect of the present invention is a lamination status inspecting apparatus that inspects a lamination status of adjacent sheets, and includes a first illumination unit that irradiates a portion where sheets are adjacent to each other with light from a predetermined direction, a second illumination unit that irradiates with light from a direction opposite to a direction of the first illumination unit, an imaging unit that picks up an image of the portion, and an imaging control unit that controls the imaging unit to pick up a first image of the portion by lighting the first illumination unit, and controls the imaging unit to pick up a second image of the portion by lighting the second illumination unit.

A lamination status inspecting method according to another aspect of the present invention is a lamination status inspecting method for inspecting a lamination status of adjacent sheets, and includes firstly picking up a first image of a portion where sheets are adjacent to each other by irradiating the portion with light from a predetermined direction, and secondly picking up a second image of the portion by irradiating the portion with light from a direction opposite to the predetermined direction.

A computer-readable recording medium according to still another aspect of the present invention is a computer-readable recording medium that stores therein a computer program that causes a computer to execute a lamination status detecting program, and the computer program causes the computer execute firstly detecting a sheet end from a first image obtained by imaging a portion where sheets are adjacent to each other by irradiating the portion with light from a predetermined direction, secondly detecting a sheet end from a second image obtained by imaging the portion by irradiating the portion with light from a direction opposite to the predetermined direction, and determining a lamination status between the sheets based on a detection result in the firstly detecting and a detection result in the secondly detecting.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 12 is a flowchart of a process procedure of a sheet-end detecting process performed by a sheet end detector;

FIG. 13 is an example of coefficients of an edge enhancement filter;

FIG. 14 is a diagram of an example of coefficients of an edge detection filter used for one picked-up image;

FIG. 15 is a diagram of an example of coefficients of an edge detection filter used for another picked-up image.

DETAILED DESCRIPTION OF THE PREFERRED EMBODIMENTS

Exemplary embodiments of a lamination status inspecting apparatus, a lamination status inspecting method, and a lamination status detecting program according to the present invention will be explained below in detail with reference to the accompanying drawings. Note that the invention is not limited to the embodiments.

Figure 1:
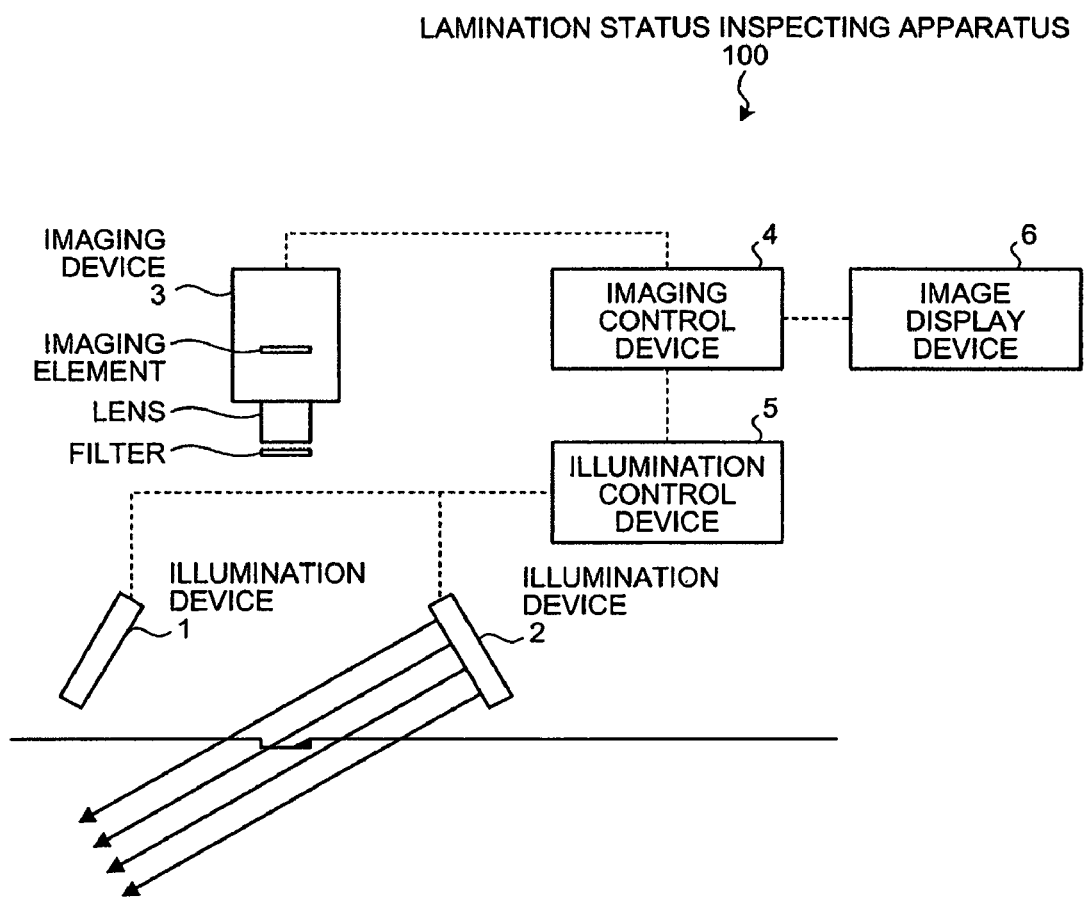
FIG. 1 is a functional block diagram of a configuration of a lamination status inspecting apparatus according to a first embodiment.

First, a configuration of a lamination status inspecting apparatus according to a first embodiment is explained. FIG. 1 is a functional block diagram of a configuration of a lamination status inspecting apparatus according to the first embodiment. As shown in FIG. 1, a lamination status inspecting apparatus 100 includes an illumination device 1, an illumination device 2, an imaging device 3, and an imaging control device 4, an illumination control device 5, and an image display device 6.

The illumination device 1 irradiates with light a portion where a sheet, which is just applied as a laminate, comes next to an adjacent sheet which is adjacent to the just-applied sheet. The illumination device 2 irradiates the portion where the just-applied sheet comes next to the adjacent sheet with light from a direction opposite to a direction of the light from the illumination device 1. As light emitting elements of the illumination device 1 and the illumination device 2, elements such as LEDs having a short rising time till light emission are used to switch over the illuminations.

The imaging device 3 picks up an image of a portion where the just-applied sheet comes next to the adjacent sheet. A CCD or a CMOS is used as an imaging element. Regarding a size of the imaging element, the number of pixels, a frame rate, a scan system, a lens, and an optical filter, optimum ones are selected depending on an inspection target and inspection performance.

Figure 2A:
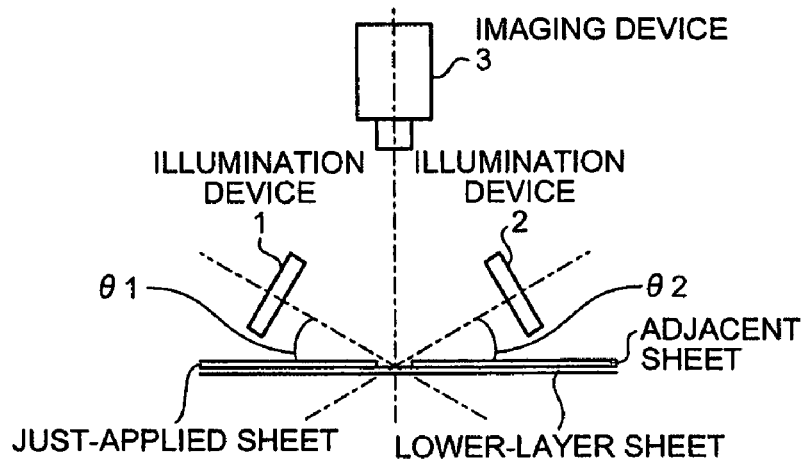
FIG. 2A is a front view of an example of a setting of two illumination devices and an imaging device of the lamination status inspecting apparatus of the first embodiment.
Figure 2B:
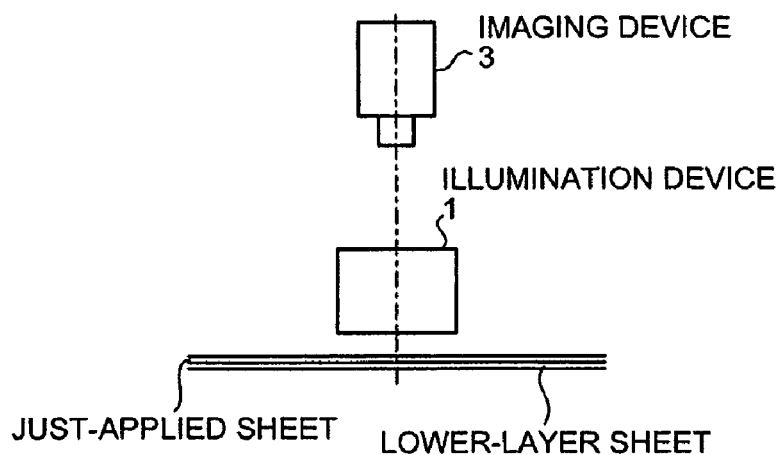
FIG. 2B is a side view of the example shown in FIG. 2A.
Figure 2C:
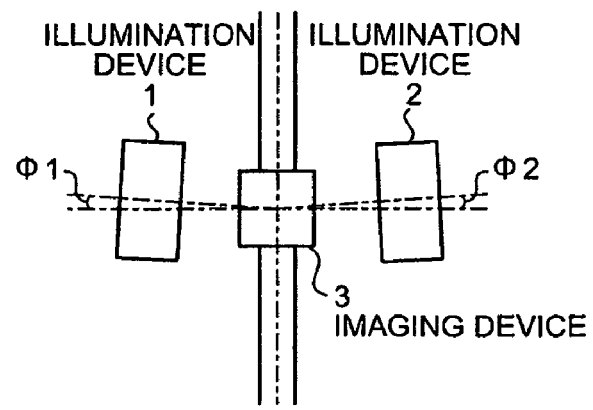
FIG. 2C is a bird's-eye view of the example shown in FIG. 2A.

FIGS. 2A, 2B, and 2C are views of an example of a setting of the illumination device 1, the illumination device 2, and the imaging device 3, and are a front view, a side view, and a bird's-eye view, respectively. As shown in FIGS. 2A, 2B, and 2C, the imaging device 3 is arranged substantially perpendicularly to the sheets, above the sheet end.

The illumination device 1 is arranged so that an angle formed between the light axis of the illumination device 1 and the sheets is θ1, and an angle between the light axis and the sheet end is Φ1, as shown in FIGS. 2A, 2B, and 2C. Here, θ1 is properly determined based on the thickness of the sheet, the number of pixels of the imaging device 3, a type of lens, and a distance between the imaging device and the sheets. Though it is desirable that Φ1 be zero, a tolerable range of Φ1 is set approximately to ±5° depending on the position of arrangement.

The illumination device 2 is arranged so that an angle formed between the light axis of the illumination device 2 and the sheets is θ2, and an angle between the light axis and the sheet end is Φ2, as shown in FIGS. 2A, 2B, and 2C. Here, θ2 and Φ2 are determined in a similar manner to that of θ1 and Φ1, and θ2=θ1 and Φ2=Φ1.

The imaging control device 4 controls imaging, for example, by controlling a shutter timing of the imaging device 3, a shutter release time, and gain. The imaging control device 4 instructs the illumination control device 5 so that the lighting of the illumination device 1 and the illumination device 2 and the shutter timing of the imaging device 3 are synchronous.

That is, the imaging control device 4 instructs the illumination control device 5 to alternately light the illumination device 1 and the illumination device 2, and also instructs the imaging device 3 to pick up an image when each illumination device is lighted. An image that the imaging device 3 picks up when the illumination device 1 is lighted is called a picked-up image$_1$, and an image that the imaging device 3 picks up when the illumination device 2 is lighted is called a picked-up image$_2$.

When the imaging control device 4 instructs the illumination control device 5 to alternately light the illumination device 1 and the illumination device 2, and also instructs the imaging device 3 to pick up an image when each illumination device is lighted, the single imaging device 3 is sufficient for picking up images formed by plural illuminations.

The illumination control device 5 controls lighting, for example, by controlling a lighting timing and a lighting time of the illumination device 1 and the illumination device 2 based on the instructions of the imaging control device 4. While the imaging control device 4 synchronizes the lighting of each illumination device and the imaging by the imaging device 3 in this example, the illumination control device 5 can synchronize the lighting of each illumination device and the imaging by the imaging device 3, and instructs the imaging timing to the imaging control device 4.

The illumination device 1 and the illumination device 2 are switched from one to another so as to alternately light up each n (n≧1) frames. When the imaging device of the interlace system is used, the lighting can be changed over for each field. In this case, even fields and odd fields are irradiated with different illuminations. When the light emitting elements that can perform pulse lighting such as an LED are employed, the light emitting timing and the light emitting time of the light emitting element are matched with the release timing and release time of the shutter of the imaging element, so as to realize efficient lighting.

The image display device 6 takes in image signals output from the imaging control device 4, and displays an image on a display. A device having a display function such as a personal computer or a television having an external input function is used for the image display device 6. The image display device 6 can directly display images by switching the images for each frame or each field, and can display two images separately as the illumination device 1 and the illumination device 2 are lighted.

Figure 3:
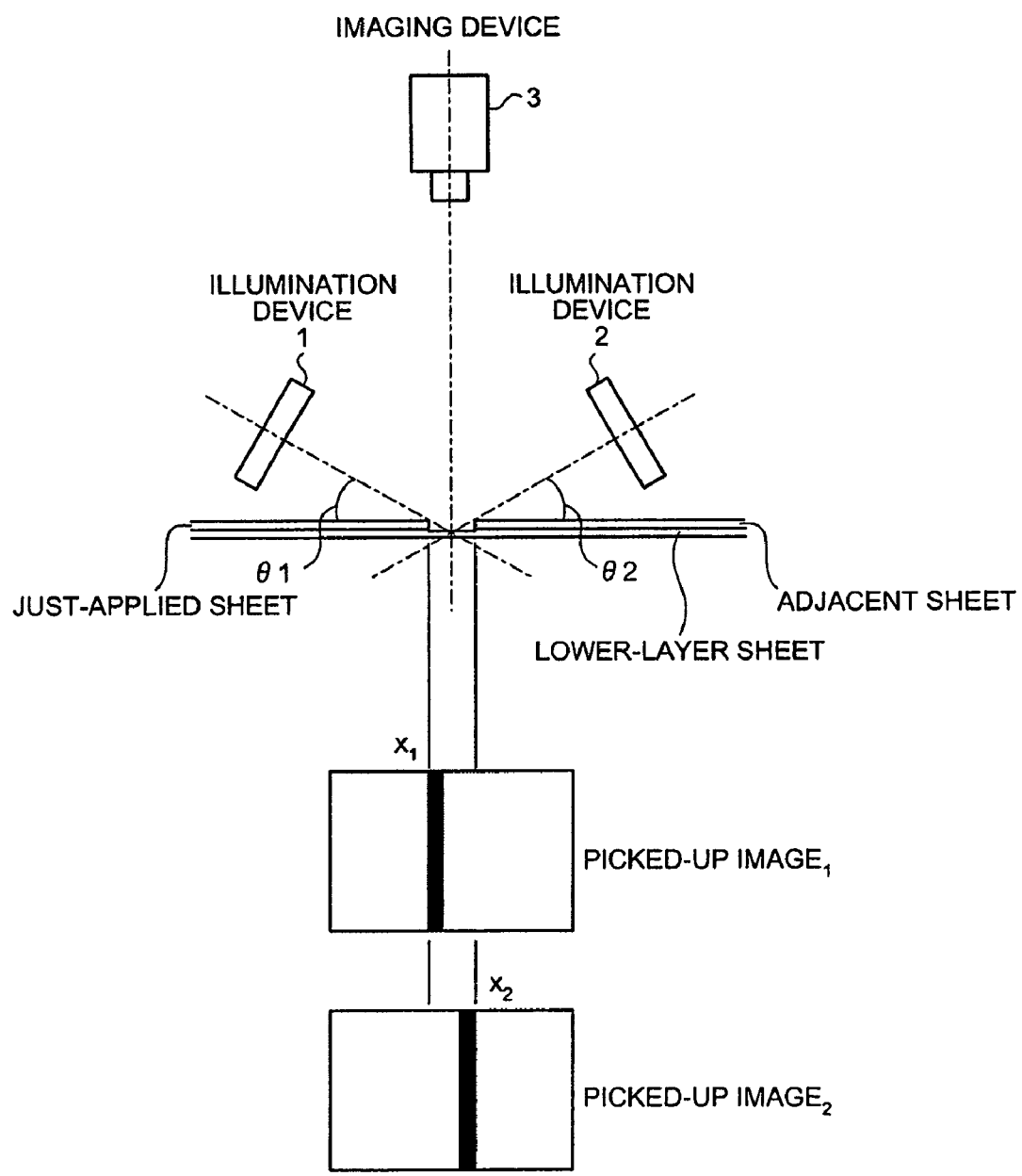
FIG. 3 is a diagram of an example of a picked-up image when there is a gap between sheets.

Examples of the picked-up image$_1$ obtained by the imaging device 3 when the illumination device 1 is lighted and the picked-up image$_2$ obtained by the imaging device 3 when the illumination device 2 is lighted are explained with reference to FIG. 3 to FIG. 5. FIG. 3 is a diagram of an example of a picked-up image when there is a gap between sheets. As shown in FIG. 3, in the picked-up image$_1$ a step between the just-applied sheet and a lower-layer sheet appears as a shade, and the left side of the shade is an end of the just-applied sheet. Similarly, in the picked-up $image_2$, a step between the adjacent sheet and the lower-layer sheet appears as a shade, and the right side of the shade is an end of the adjacent sheet. When the gap between the just-applied sheet and the adjacent sheet is accommodated within a screen, the sheet end can be confirmed in both images as shown in FIG. 3.

For the screen shown in FIG. 3, an origin of the coordinates of the screen is set to an upper left point as (x, y)=(0, 0). A position of the sheet end is represented by the x-coordinate. Specifically, a position of the sheet end detected in the picked-up $image_1$ is expressed by its x-coordinate $x_1$, and a position of the sheet end detected in the picked-up $image_2$ is expressed by its x-coordinate $x_2$.

Figure 4:
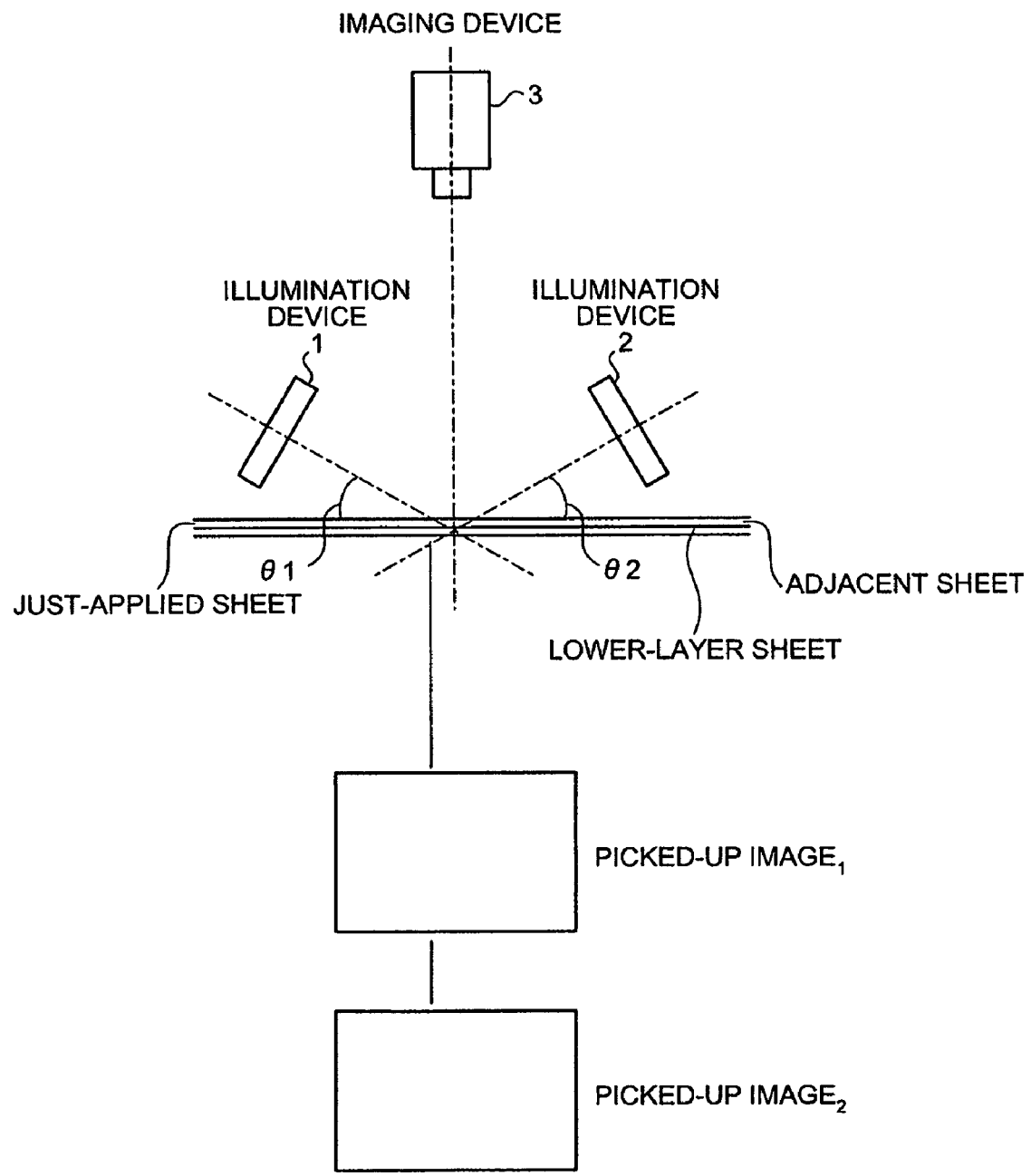
FIG. 4 is a diagram of an example of a picked-up image when there is no gap between sheets.

FIG. 4 is a diagram of an example of a picked-up image when there is no gap between the sheets. As shown in FIG. 4, when there is no gap between the sheets, the sheet end cannot be confirmed in either one of the images.

Figure 5:
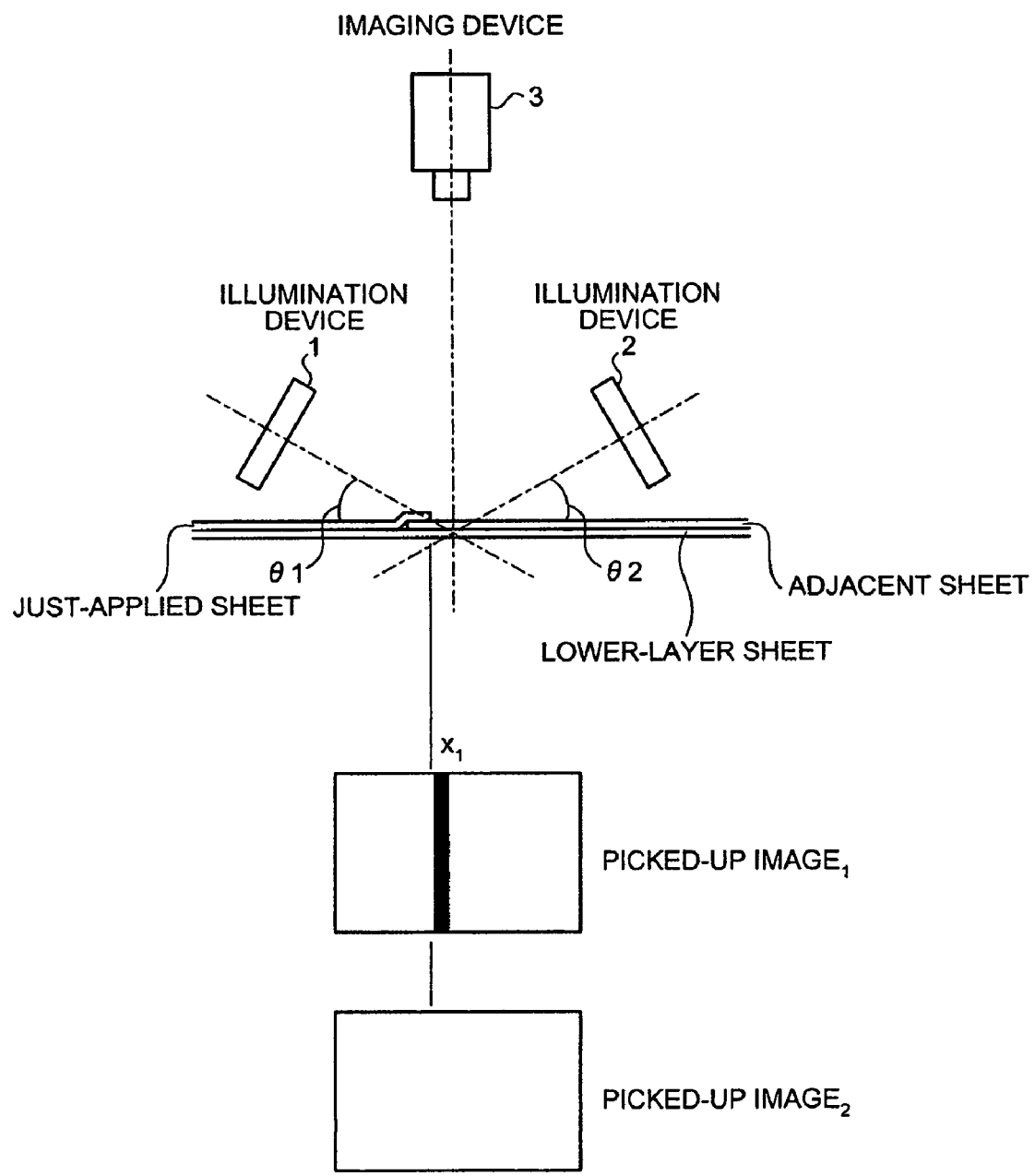
FIG. 5 is a diagram of an example of a picked-up image when sheets are overlapped with each other.

FIG. 5 is a diagram of an example of a picked-up image when sheets are overlapped with each other. As shown in FIG. 5, when the just-applied sheet extends over the adjacent sheet, a step appears as a shade in the picked-up $image_1$, and no shade can be confirmed in the picked-up $image_2$. When there is no adjacent sheet or when a gap between the just-applied sheet and the adjacent sheet cannot be accommodated in the screen, a shade sometimes cannot be confirmed in the picked-up $image_2$ similarly to the example shown in FIG. 5.

As described above, in the first embodiment, the imaging control device 4 controls so that the imaging device 3 picks up an image of a portion where the just-applied sheet lies side by side with the adjacent sheet, by irradiating the portion alternately with the light from the illumination device 1 and the light from the illumination device 2. Therefore, a compact device can inspect the lamination status of the sheets without using a mirror, two light-receiving sensors, and two lenses.

While the first embodiment explains the case where the image display device 6 displays the images picked up by the imaging device 3, a lamination status of sheets can be also automatically determined by processing the images picked up by the imaging device 3. A second embodiment explains a lamination status inspecting device that automatically determines a lamination status of sheets by processing the images picked up by the imaging device 3.

Figure 6:
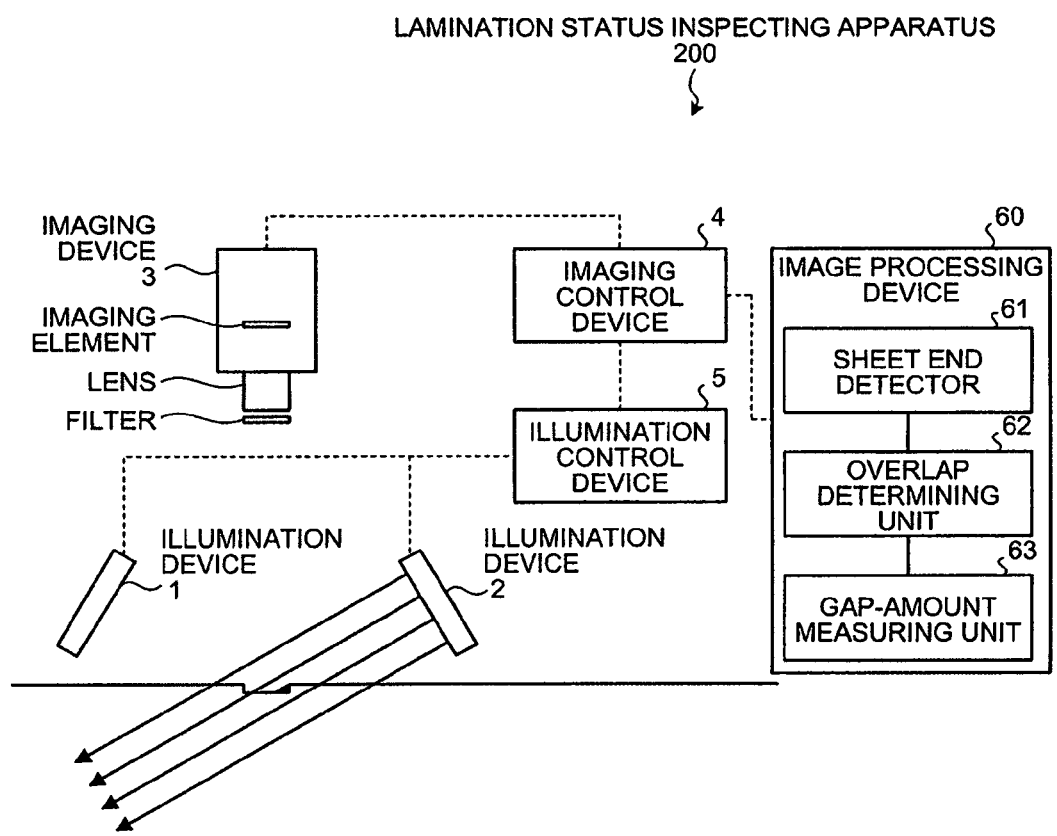
FIG. 6 is a functional block diagram of a configuration of a lamination status inspecting apparatus according to a second embodiment.

Firstly, a configuration of the lamination status inspecting device according to the second embodiment is explained. FIG. 6 is a functional block diagram of a configuration of the lamination status inspecting apparatus according to the second embodiment. Functional units that operate similarly to those of the units in FIG. 1 are denoted by like reference numerals, and detailed explanations thereof will not be repeated for the convenience of description.

As shown in FIG. 6, a lamination status inspecting device 200 includes the illumination device 1, the illumination device 2, the imaging device 3, the imaging control device 4, the illumination control device 5, and an image processing device 60. The image processing device 60 automatically determines a lamination status of sheets by processing images picked up by the imaging device 3, and includes a sheet end detector 61, an overlap determining unit 62, and a gap-amount measuring unit 63.

The sheet end detector 61 is a processing unit that detects a sheet end by processing images picked up by the imaging device 3. Specifically, the sheet end detector 61 detects a sheet end, using a shade generated in the picked-up $image_1$ and the picked-up $image_2$ shown in FIG. 3 to FIG. 5.

The overlap determining unit 62 is a processing unit that determines whether there is an overlap or a gap between a just-applied sheet and an adjacent sheet based on a sheet end detected by the sheet end detector 61. Specifically, when a sheet end is detected in both the picked-up $image_1$ and the picked-up $image_2$, the overlap determining unit 62 determines that there is a gap between the just-applied sheet and the adjacent sheet. When a sheet end is detected in the picked-up $image_1$ and is not detected in the picked-up $image_2$, the overlap determining unit 62 determines that the just-applied sheet is overlapped with the adjacent sheet. When a sheet end is not detected from any of the picked-up $image_1$ and the picked-up $image_2$, the overlap determining unit 62 determines that the just-applied sheet lies next to the adjacent sheet without a gap.

The gap-amount measuring unit 63 is a processing unit that calculates a gap amount when the overlap determining unit 62 determines that there is a gap between the just-applied sheet and the adjacent sheet. Specifically, the gap-amount measuring unit 63 calculates a difference between $x_2$ and $x_1$ shown in FIG. 3 as a gap amount.

In the above, the sheet end detector 61 detects a sheet end using shades shown in FIG. 3 to FIG. 5. However, a sheet end cannot be detected using a shade in some cases. A method of detecting a sheet end when a sheet end cannot be detected using a shade is explained next.

Assume that a laminate sheet is a carbon sheet. The carbon sheet has a characteristic that when the sheet is irradiated with light from a direction perpendicular to a fiber direction, reflection of the light is strong, and that when the sheet is irradiated with light from the same direction as the fiber direction, reflection of the light is weak. Since the sheets are arranged in the fiber direction in lamination, in detecting an overlap or a gap between sheets to be inspected, it is sufficient if the sheet is always irradiated with light from a direction perpendicular to the fiber direction. In this case, a contrast between the shade portion and other sheet portion is strong. Therefore, a sheet end can be detected easily. In some cases, an entire portion of the gap has a significantly low brightness because of a difference of fiber direction of the laminate sheet and the adjacent sheet, and the gap cannot be distinguished from a shade. Even in such case, if a method of detecting an edge is used, the gap can be detected by the same detecting method as that of detecting only a shade.

However, a lamination device often laminates sheets in dozens of layers and hundreds of layers, and inspected sheets are sometimes dozens of meters in size. Therefore, when a device independent of the lamination device performs inspections alone, a very long time is required. Further, if the inspection is performed by a device independent from the lamination device, a structure must be formed so that the lamination status inspecting apparatus and the inspected object can be transported during a sheet lamination process of the inspected objects for the measurement of an overlap and a gap amount of adjacent sheets, which is very inefficient. Accordingly, it is necessary to fit the lamination status inspecting apparatus to the lamination device to eliminate the need of taking time for the inspection in addition to the time for lamination by simultaneously performing lamination and inspection.

Figure 7:
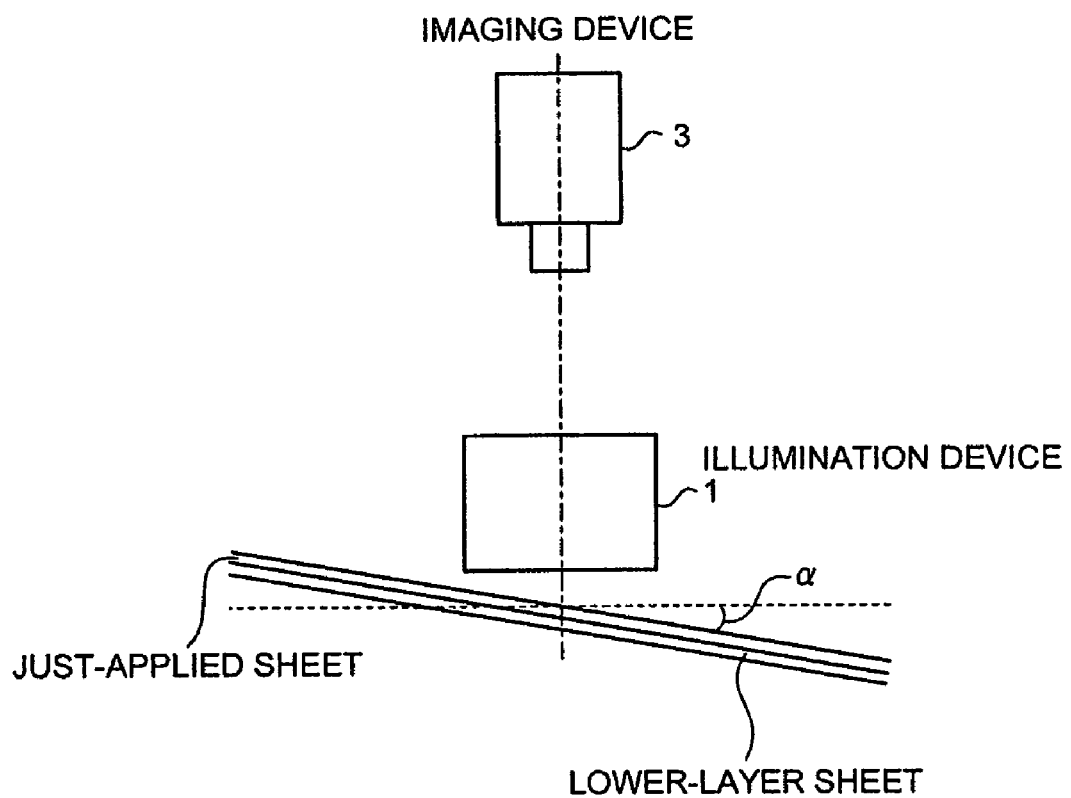
FIG. 7 is a side view of a lamination status inspecting apparatus when sheets have an inclination.

However, when the lamination status inspecting apparatus is fitted to the lamination device, there is a drawback in that the sheet to be detected, the illuminations, and the camera cannot be always held in a constant positional relationship. The lamination device laminates sheets with a roller, and therefore can laminate the sheets without inclining the axis when laminating sheets on the lamination surface of an upward slope or a downward slope. Therefore, unless the lamination status inspecting apparatus has a system that can constantly keep the sheets, the illuminations, and the camera in a predetermined positional relationship following the upward slope or the downward slope, the sheets can be inclined relative to the imaging device and the illumination device as shown in FIG. 7.

When the sheets are inclined as described above, the following changes occur in the image picked up by the imaging device.

(1) Because an angle formed between the fiber direction of the sheet and the illumination direction is not a right angle, brightness of the sheet lowers as the inclination angle increases.

(2) Because a step in the sheets is irradiated by illuminations, reflection from the step is stronger than that from other portions. Therefore, brightness is kept high even when the sheets are inclined.

Figure 8:
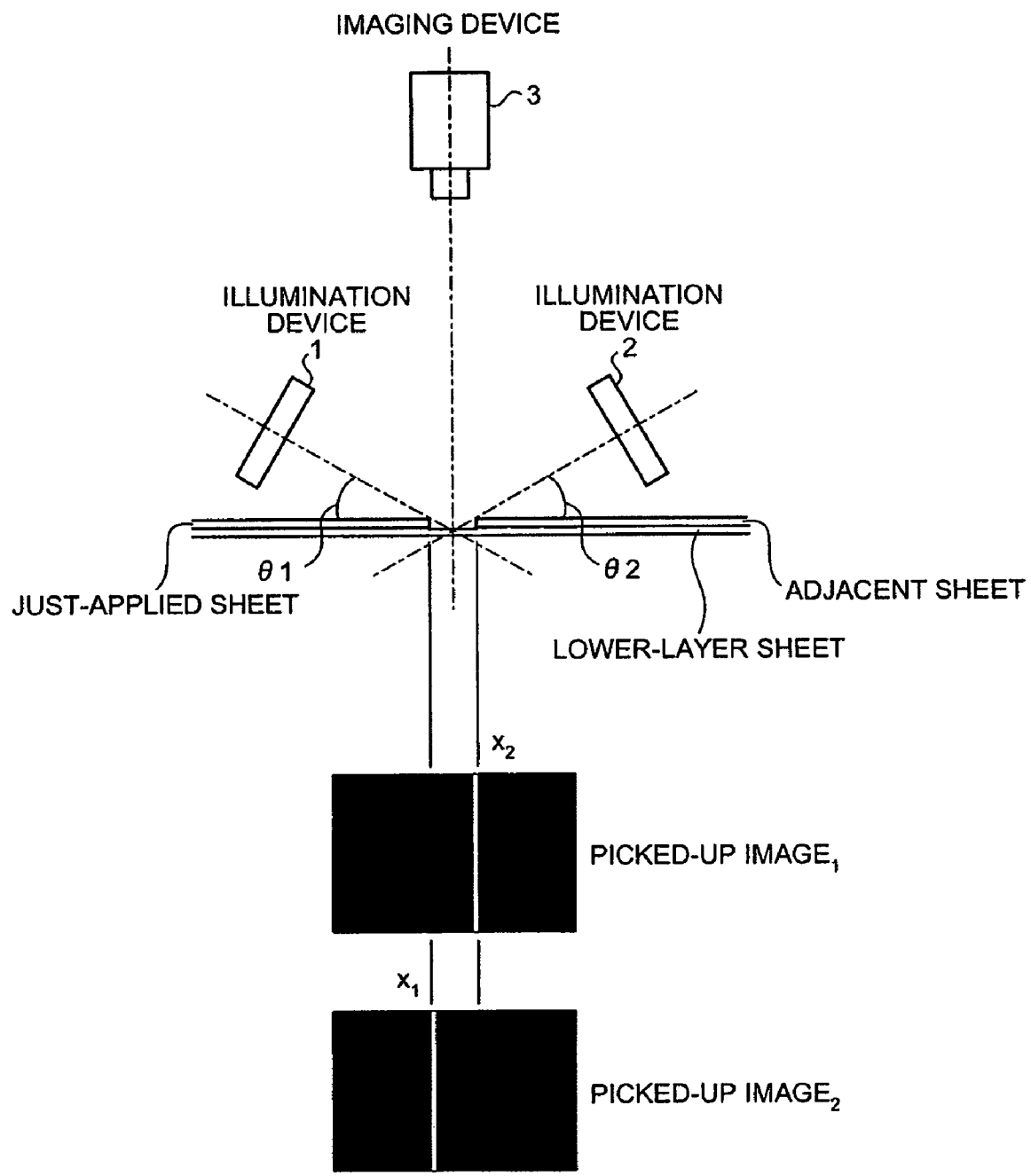
FIG. 8 is a diagram of an example of a picked-up image when there is a gap between inclined sheets.
Figure 9:
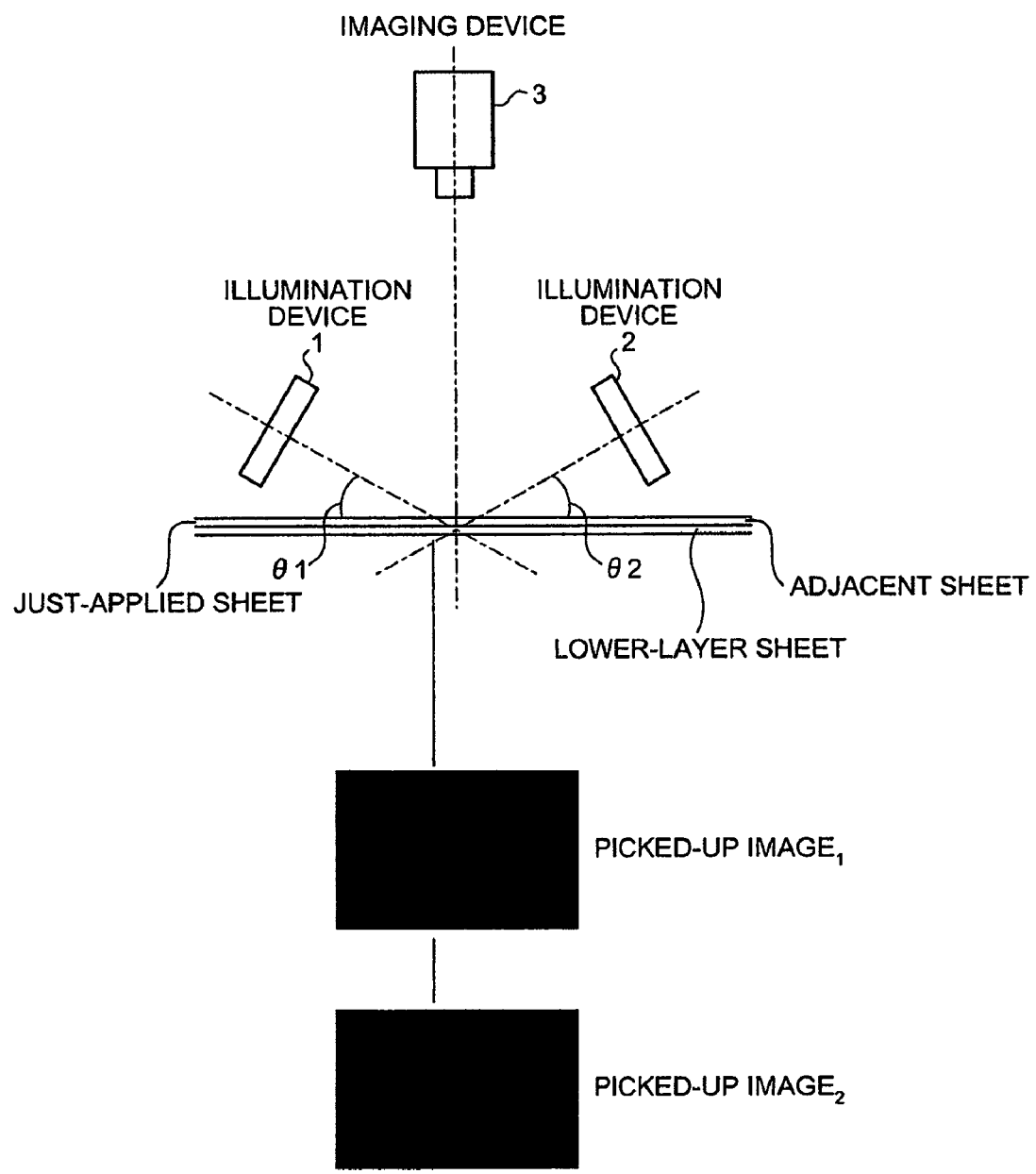
FIG. 9 is a diagram of an example of a picked-up image when there is no gap between inclined sheets.
Figure 10:
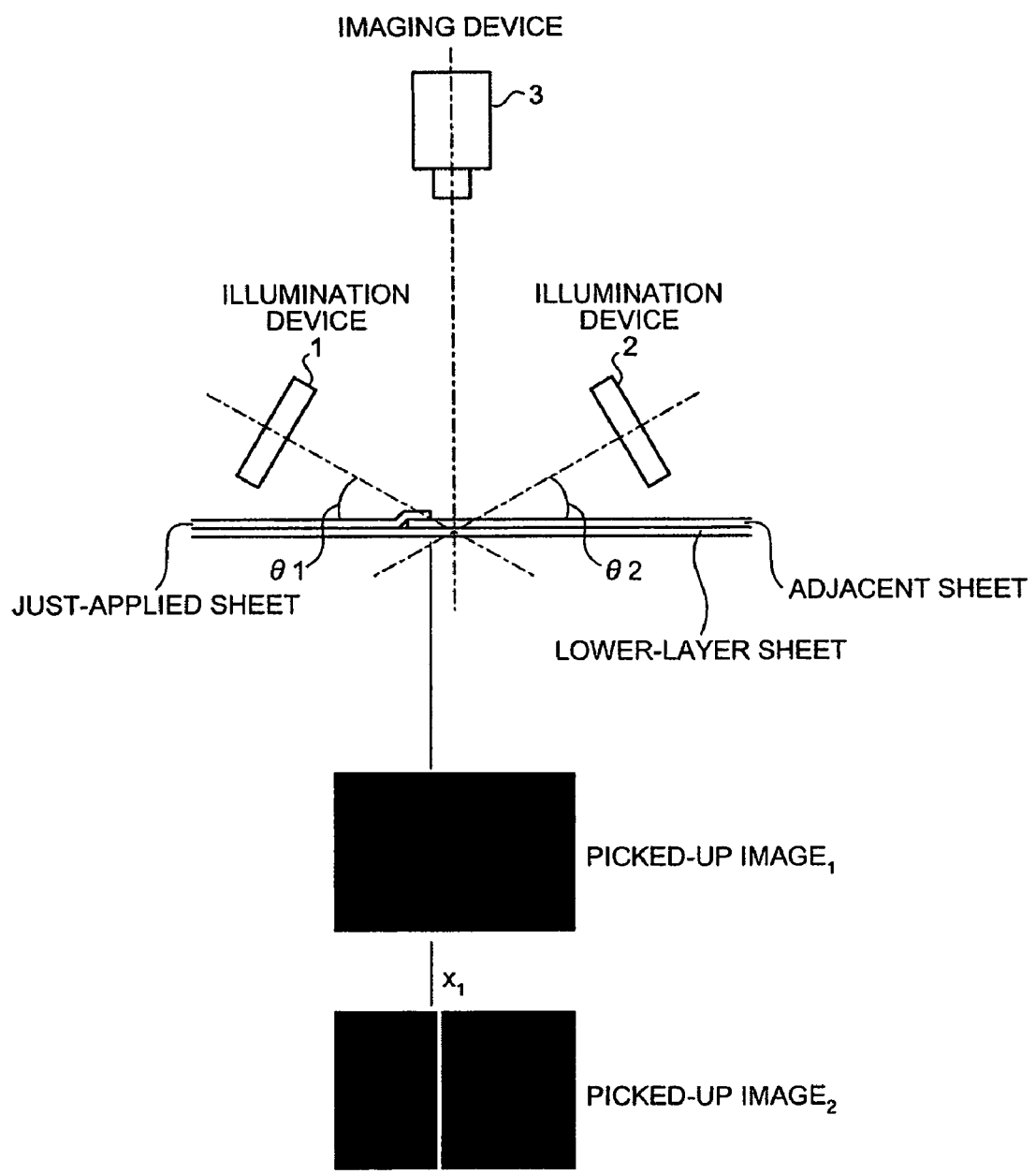
FIG. 10 is a diagram of an example of a picked-up image when there is an overlap of inclined sheets.

Because of (1) and (2), when the sheets are inclined, an image having high brightness only in a step portion is obtained, as shown in FIG. 8 to FIG. 10. FIG. 8 is a diagram of an example of a picked-up image when there is a gap between inclined sheets. FIG. 9 is a diagram of an example of a picked-up image when there is no gap between inclined sheets. FIG. 10 is a diagram of an example of a picked-up image when there is an overlap of inclined sheets.

When sheets are inclined, edges obtained from the picked-up $image_1$ and the picked-up $image_2$ are at opposite positions from those detected based on the shades. Specifically, the sheet end detector 61 detects the sheet end $x_2$ from the picked-up $image_1$ and detects the sheet end $x_1$ from the picked-up $image_2$.

When only the step portion has high brightness, an inclination angle α depends on a size of and a distance from the illumination. When the illumination is made larger or is brought nearer, the inclination angle α becomes larger, whereas when the illumination is made smaller or is brought farther, the inclination angle α becomes smaller.

In FIG. 7, the brightness of the sheets becomes gradually lower when the inclination angle α becomes large. Therefore, it is possible to fit the lamination status inspecting apparatus to the lamination device so that the imaged sheets is always in a same fiber direction within a predetermined region (hereinafter referred to as "region S") of a picked-up image, and to switch a manner of detection between two manners depending on an average brightness of the region S: according to one manner, the detection is performed utilizing the shade generated in a step portion; according to another manner, the detection is performed utilizing the fact that the brightness increases only in the step portion.

Specifically, when average brightness of the region S is equal to or higher than a threshold value, the sheet end $x_1$ is detected using the picked-up image, and the sheet end $x_2$ is detected using the picked-up $image_2$. On the other hand, when average brightness of the region S is not equal to or higher than a threshold value, the sheet end $x_2$ is detected using the picked-up image, and the sheet end $x_1$ is detected using the picked-up $image_2$.

Figure 11:
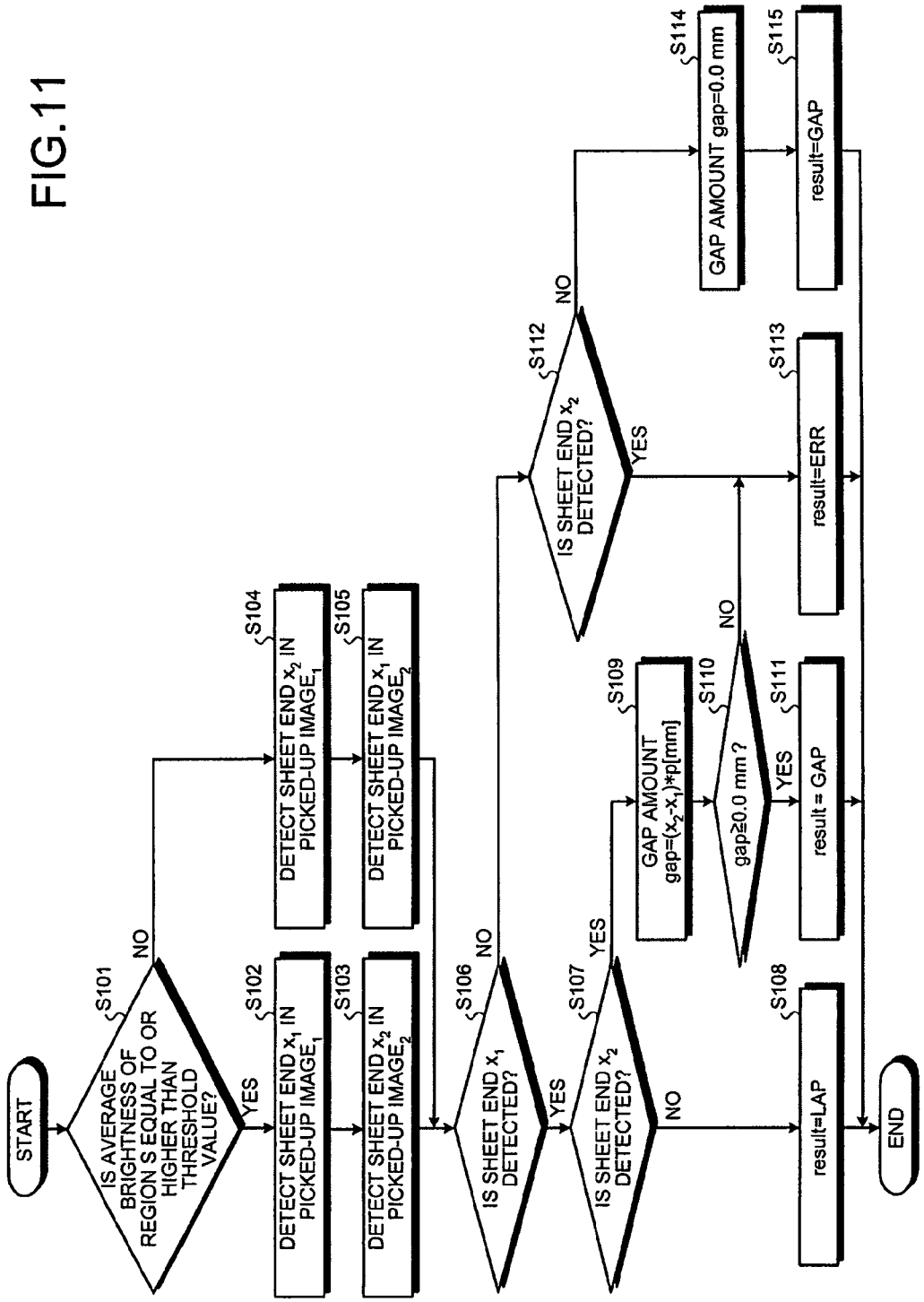
FIG. 11 is a flowchart of a process procedure of a lamination status detecting process performed by an image processing device.

A process procedure of the lamination status detecting process performed by the image processing device 60 is explained next. FIG. 11 is a flowchart of a process procedure of the lamination status detecting process performed by the image processing device 60. This lamination status detecting process is performed each time the picked-up $image_1$ and the picked-up $image_2$ are taken in.

As shown in FIG. 11, the overlap determining unit 62 of the image processing device 60 determines whether the average brightness of the region S is equal to or higher than a threshold value (step S101). When the average brightness of the region S is equal to or higher than the threshold value, the sheet end detector 61 detects the sheet end $x_1$ in the picked-up $image_1$ (step S102), and detects the sheet end $x_2$ in the picked-up $image_2$ (step S103). On the other hand, when the average brightness of the region S is lower than the threshold value, the sheet end detector 61 detects the sheet end $x_2$ in the picked-up $image_1$ (step S104), and detects the sheet end $x_1$ in the picked-up $image_2$ (step S105).

The overlap determining unit 62 determines whether the sheet end $x_1$ is detected (step S106). When the sheet end $x_1$ is detected, the overlap determining unit 62 determines whether the sheet end $x_2$ is detected (step S107). When the sheet end $x_2$ is not detected as a result, the sheets are overlapped with each other. Therefore, a result of the determination is set as "overlapped" (result=LAP) (step S108).

On the other hand, when the sheet end $x_2$ is detected, the gap-amount measuring unit 63 calculates a gap amount (gap) using a difference between $x_2$ and $x_1$ (step S109). When a lateral width of an imaging range of the imaging device 3 is w [mm], and the number of pixels in the lateral direction of the image is represented as "width", gap=$(x_2-x_1)$*p=$(x_2-x_1)$*w/width.

The overlap determining unit 62 determines whether the gap amount is equal to or larger than 0.0 mm (step S10). When the gap amount is equal to or larger than 0.0 mm, a gap is present between the sheets. Therefore, a result of determination is set to "there is gap" (result=GAP) (step S111). When the gap amount is smaller than 0.0 mm, there is an abnormality in the detection of the sheet end. Therefore, a result of determination is set to "error" (result=ERR) (step S113).

When the sheet end $x_1$ is not detected, the overlap determining unit 62 determines whether the sheet end $x_2$ is detected (step S112). When the sheet end $x_2$ is detected, the just-applied sheet is not beneath the adjacent sheet, and the sheet end is not properly detected. Therefore, a result of determination is set to "error" (result=ERR) (step S113). When the sheet end $x_2$ is not detected, there is no gap between the sheets. Therefore, the gap amount is set to 0.0 mm (step S114), and a result of determination is set to "there is gap" (result=GAP) (step S115).

As explained above, since the overlap determining unit 62 determines a gap and an overlap between the sheets based on a result of the sheet end detection by the sheet end detector 61, a lamination status of the sheets can be inspected.

Next, a process procedure of a sheet-end detecting process performed by the sheet end detector 61 is explained. FIG. 12 is a flowchart of a process procedure of the sheet-end detecting process performed by the sheet end detector 61. As shown in FIG. 12, the sheet end detector 61 applies an edge enhancement filter to a picked-up image (step S201).

The edge enhancement filter is a filter of coefficients as shown in FIG. 13, for example. When a pixel concerned is f(x, y), a pixel value g(x, y) after the edge enhancement filter is applied can be represented by the following equation (1).

$$g(x, y) = \sum_{i=x-1}^{x+1} \sum_{j=y-1}^{y+1} k_{i,j} * f(i, j) \qquad (1)$$

An edge detection filter is applied to the image to which the edge enhancement filter is applied (step S202). For the picked-up $image_1$ the edge detection filter is a filter of coefficients as shown in FIG. 14, for example, and for the picked-up $image_2$, the edge detection filter is a filter of coefficients as shown in FIG. 15, for example.

The image to which the edge detection filter is applied is binarized (step S203). A predetermined threshold value can be used for the binarization. Alternatively, a gradation histogram can be generated, and a threshold value may be set to a gradation value of higher 5% of a total number of pixels of an image so that the threshold value is variable. When the threshold value is th, and a pixel concerned is f(x, y), a binarized pixel value g(x, y) can be represented by the following equation (2).

$$g(x, y) = \begin{cases} 1 (\text{when } f(x, y) \geq th) \\ 0 (\text{except above}) \end{cases} \quad (2)$$

The binarized image is projected in a perpendicular direction (step S204), and a histogram is generated. When the binarized pixel value is f(x, y), a histogram h(x) is obtained by the following equation (3), where "height" is the number of pixels in a vertical direction of the image.

$$h(x) = \sum_{y=0}^{height-1} f(x, y) \quad (3)$$

Lastly, the sheet end positions $x_1$ and $x_2$ are calculated using the histogram h(x) (step S205). In calculating the position $x_1$ of the sheet end in the picked-up image$_1$, the value of h(x) is checked starting from x=0 in an ascending order, and when h(x) shows a peak value equal to or higher than a predetermined threshold value for the first time, a corresponding "x" is set as the position x1 of the sheet end. In calculating the position $x_2$ of the sheet end in the picked-up image$_2$, the value of h(x) is checked starting from x=width−1 (where width represents the number of pixels in the lateral direction) in a descending order, and when h(x) shows a peak value equal to or higher than a predetermined threshold value for the first time, a corresponding "x" is set as the position x2 of the sheet end.

In calculating the position $x_2$ of the sheet end in the picked-up image$_1$, filter coefficients shown in FIG. 14 are used as the edge detection filter, and the value of h(x) is checked starting from x=width−1 in a descending order, and when the value of h(x) takes a peak value equal to or higher than a predetermined threshold value for the first time, a corresponding "x" is set as the position $x_2$ of the sheet end. In calculating the position $x_1$ of the sheet end in the picked-up image$_2$, filter coefficients shown in FIG. 15 are used as the edge detection filter, and the value of h(x) is checked starting from x=0 in an ascending order, and when the value of h(x) takes a peak value equal to or higher than a predetermined threshold value for the first time, a corresponding "x" is set as the position $x_1$ of the sheet end.

As described above, in the second embodiment, the sheet end detector 61 of the image processing device 60 detects a sheet end from the picked-up image, and the overlap determining unit 62 determines a gap and an overlap between sheets based on the sheet end detected by the sheet end detector 61. Thus, a sheet lamination status can be inspected.

In the second embodiment, the overlap determining unit 62 determines whether the average brightness of the region S of the picked-up image is equal to or higher than a predetermined threshold value. When the average brightness of the region S of the picked-up image is not lower than a predetermined threshold value, the sheet end is detected based on a fact that the brightness is high only in the step portion of the sheet. Therefore, the sheet end can be detected in high precision even when the sheets are in an inclined state.

In the second embodiment, the image processing device 60 that operates as a lamination status detecting device detecting a lamination status is explained. Further, a lamination status detecting program having a similar function can be also obtained by realizing the configuration of the image processing device 60 by software. A computer that executes this lamination status detecting program is explained next.

Figure 16:
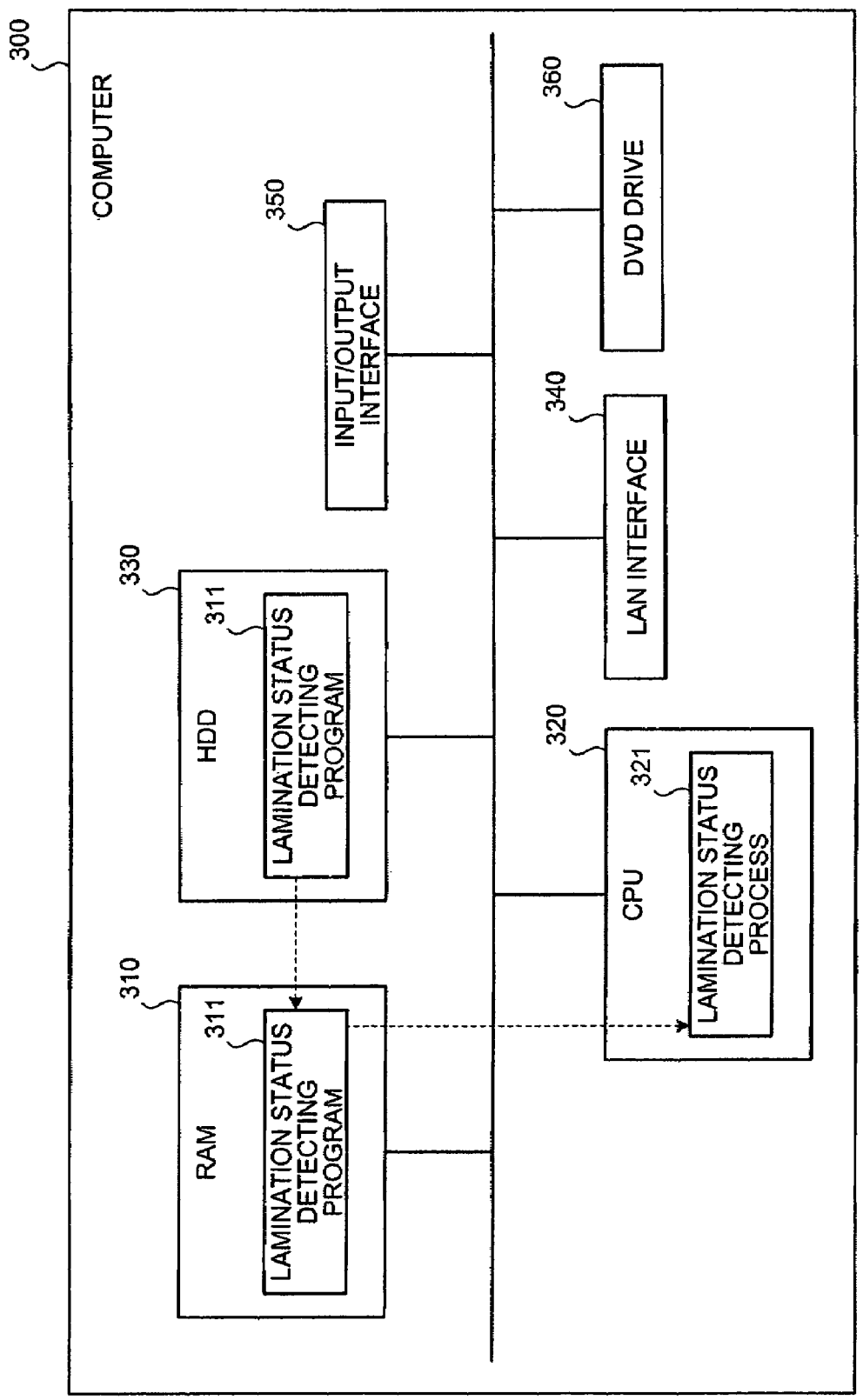
FIG. 16 is a functional block diagram of a configuration of a computer executing a lamination status detecting program according to the second embodiment.

FIG. 16 is a functional block diagram of a configuration of a computer executing the lamination status detecting program according to the second embodiment. As shown in FIG. 16, a computer 300 includes a RAM 310, a CPU 320, an HDD 330, a LAN interface 340, an input/output interface 350, and a DVD drive 360.

The RAM 310 is a memory storing programs and an intermediate result of the execution of a program. The CPU 320 is a central processing unit reading a program from the RAM 310 and executing the program.

The HDD 330 is a disk device storing programs and data. The LAN interface 340 is an interface for connecting the computer 300 to other computer via a LAN.

The input/output interface 350 is an interface for connecting an input unit and a display unit such as a mouse and a keyboard. The DVD drive 360 is a device for reading and writing of the DVD.

A lamination status detecting program 311 executed by the computer 300 is stored in the DVD. The DVD drive 360 reads the lamination status detecting program 311 from the DVD, and installs the read program into the computer 300.

Alternatively, the lamination status detecting program 311 is stored in a database of other computer system connected via the LAN interface 340, and is read from this database and is installed into the computer 300.

The installed lamination status detecting program 311 is stored in the HDD 330, and is read out to the RAM 310. The CPU 320 executes the read program as a lamination status detecting process 321.

In the first embodiment and the second embodiment, inspection of a gap and an overlap between sheets is explained. However, the present invention is not limited thereto, and the invention can also be similarly applied to the inspection of a gap, an overlap, and a level difference between objects other than the sheets.

According to the embodiments as described above, no mirror is required, and one light-receiving sensor and one lens are sufficient. Therefore, there is an effect that the lamination status can be inspected with a compact apparatus.

According to the embodiments as described above, an inspection of a lamination status can be automated without depending on a manual work. Therefore, there is an effect that inspection precision can be improved and inspection cost and inspection time can be decreased.

According to the embodiments as described above, a sheet end is detected even when the brightness is low. Therefore, there is an effect that a lamination status can be determined even when a reflection light from the sheet is weak because of, for example, the inclination of the sheet.

As described above, the lamination status inspecting apparatus, the lamination status inspecting method, and the lamination status detecting program according to the present invention are useful for manufacturing a molded product by laminating sheets, and are particularly suitable when a gap and an overlap between the sheets significantly affect the quality of the molded product.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A lamination status inspecting apparatus that inspects a lamination status of adjacent sheets, comprising:
   a first illumination unit that irradiates a portion where sheets are adjacent to each other with light from a predetermined direction;
   a second illumination unit that irradiates with light from a direction opposite to a direction of the first illumination unit;
   an imaging unit that picks up an image of the portion; and
   an imaging control unit that controls the imaging unit to pick up a first image of the portion by lighting the first illumination unit, and controls the imaging unit to pick up a second image of the portion by lighting the second illumination unit.

2. The lamination status inspecting apparatus according to claim 1, further comprising
   a sheet end detector that detects a sheet end from the first image and the second image, and
   a lamination status determining unit that determines a lamination status between the sheets based on a detection result of the sheet end by the sheet end detector.

3. The lamination status inspecting apparatus according to claim 2, wherein when brightness of an image is equal to or higher than a predetermined threshold value, the sheet end detector detects the sheet end using a shade generated from a step in the portion, and when the brightness of the image is lower than the predetermined threshold value, the sheet end detector detects the sheet end using an image portion having higher brightness than brightness of a surrounding portion when a step is present in the portion.

4. A lamination status inspecting method for inspecting a lamination status of adjacent sheets, comprising:
   firstly picking up a first image of a portion where sheets are adjacent to each other by irradiating the portion with light from a predetermined direction; and
   secondly picking up a second image of the portion by irradiating the portion with light from a direction opposite to the predetermined direction.

5. The lamination status inspecting method according to claim 4, further comprising
   detecting a sheet end from the first image and the second image, and
   determining a lamination status between the sheets based on a detection result in the detecting.

6. The lamination status inspecting method according to claim 5 wherein
   in the detecting, the sheet end is detected using a shade generated from a step in the portion when brightness of an image is equal to or higher than a predetermined threshold value, and the sheet end is detected using an image portion having higher brightness than brightness of a surrounding portion when a step is present in the portion when the brightness of the image is lower than the predetermined threshold value.

7. A computer-readable recording medium that stores therein a computer program that causes a computer to execute a lamination status detecting program, the computer program causing the computer execute:
   firstly detecting a sheet end from a first image obtained by picking up an image of a portion where sheets are adjacent to each other by irradiating the portion with light from a predetermined direction;
   secondly detecting a sheet end from a second image obtained by picking up an image of the portion by irradiating the portion with light from a direction opposite to the predetermined direction; and
   determining a lamination status between the sheets based on a detection result in the firstly detecting and a detection result in the secondly detecting.

8. The computer-readable recording medium according to claim 7, wherein
   in the firstly and secondly detecting, the sheet end is detected using a shade generated from a step in the portion when brightness of an image is equal to or higher than a predetermined threshold value, and the sheet end is detected using an image portion having higher brightness than brightness of a surrounding portion when a step is present in the portion when the brightness of the image is lower than the predetermined threshold value.

* * * * *